(12) United States Patent
Anderheggen et al.

(10) Patent No.: US 11,033,477 B2
(45) Date of Patent: *Jun. 15, 2021

(54) BLONDING AGENT AND METHOD FOR GENTLE OXIDATIVE HAIR LIGHTENING

(71) Applicant: Henkel AG & Co. KGaA, Duesseldorf (DE)

(72) Inventors: Bernd Anderheggen, Moenchengladbach (DE); Burkhard Mueller, Duesseldorf (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 699 days.

This patent is subject to a terminal disclaimer.

(21) Appl. No.: 15/610,195

(22) Filed: May 31, 2017

(65) Prior Publication Data

US 2017/0340549 A1 Nov. 30, 2017

Related U.S. Application Data

(60) Provisional application No. 62/345,092, filed on Jun. 3, 2016.

(30) Foreign Application Priority Data

May 31, 2016 (DE) .......................... 102016209471.8

(51) Int. Cl.

| | | |
|---|---|---|
| *A61Q 5/08* | (2006.01) | |
| *A61K 8/81* | (2006.01) | |
| *A61K 8/49* | (2006.01) | |
| *A61Q 5/10* | (2006.01) | |
| *A61K 8/02* | (2006.01) | |
| *A61K 8/22* | (2006.01) | |
| *A61K 8/19* | (2006.01) | |
| *A61K 8/23* | (2006.01) | |
| *A61K 8/24* | (2006.01) | |
| *A61K 8/25* | (2006.01) | |
| *A61K 8/31* | (2006.01) | |
| *A61K 8/362* | (2006.01) | |
| *A61K 8/41* | (2006.01) | |
| *A61K 8/44* | (2006.01) | |
| *A61K 8/60* | (2006.01) | |
| *A61K 8/73* | (2006.01) | |

(52) U.S. Cl.
CPC ............ *A61K 8/8152* (2013.01); *A61K 8/022* (2013.01); *A61K 8/0225* (2013.01); *A61K 8/19* (2013.01); *A61K 8/22* (2013.01); *A61K 8/23* (2013.01); *A61K 8/24* (2013.01); *A61K 8/25* (2013.01); *A61K 8/31* (2013.01); *A61K 8/362* (2013.01); *A61K 8/41* (2013.01); *A61K 8/44* (2013.01); *A61K 8/4946* (2013.01); *A61K 8/604* (2013.01); *A61K 8/731* (2013.01); *A61Q 5/08* (2013.01); *A61Q 5/10* (2013.01); *A61K 2800/882* (2013.01)

(58) Field of Classification Search
None
See application file for complete search history.

(56) References Cited

U.S. PATENT DOCUMENTS

| | | | | |
|---|---|---|---|---|
| 2006/0269492 A1* | 11/2006 | Narasimhan | ............. | A61K 8/23 424/62 |
| 2011/0119840 A1* | 5/2011 | Gardlik | .................... | A61K 8/22 8/408 |

FOREIGN PATENT DOCUMENTS

| | | |
|---|---|---|
| DE | 10051774 A1 | 4/2002 |
| EP | 0778020 A1 | 6/1997 |
| EP | 1034777 A1 | 9/2000 |
| EP | 1174112 A2 | 1/2002 |
| EP | 1380287 A1 | 1/2004 |
| WO | 2005115314 A1 | 12/2005 |

\* cited by examiner

*Primary Examiner* — Jyothsna A Venkat
(74) *Attorney, Agent, or Firm* — James J. Cummings

(57) ABSTRACT

A combination of at least one select dicarboxylic acid having 2 to 10 carbon atoms, in combination with at least one amino acid, selected from arginine, lysine, histidine or at least one of the salts of these amino acids, are included in a blonding powder to reduce the damage caused to keratin fibers by an oxidative bleaching treatment.

6 Claims, No Drawings

BLONDING AGENT AND METHOD FOR GENTLE OXIDATIVE HAIR LIGHTENING

FIELD OF THE INVENTION

The present invention generally relates to blonding powders used as agents for lightening keratin fibers, and in particular human hair. The present invention further relates to the use of the agents for gentle blonding or oxidative lightening of human hair, and to a multi-component packaging unit (kit of parts) for lightening keratin fibers, which comprises a blonding powder and, separately therefrom, an oxidizing agent preparation.

BACKGROUND OF THE INVENTION

Lightening one's hair color has always been a desire of many consumers since a blond hair color is perceived to be attractive and desirable from a fashion point of view. For this purpose, various blonding agents providing varying blonding performance are available on the market. The oxidizing agents present in these products are capable of lightening the hair fiber by oxidatively destroying melanin, the hair's own pigment. For a moderate blonding effect, it is sufficient to use only hydrogen peroxide—optionally with the use of ammonia or other alkalizing agents—as the oxidizing agent. To achieve a stronger blonding effect, a mixture of hydrogen peroxide and at least one compound, selected from percarbonates and persalts, and in particular peroxodisulfate salts and/or peroxomonosulfate salts, is typically used. So as to enhance the blonding action, the agents have higher concentrations of hydrogen peroxide and percarbonates or persalts, and in particular persulfates. In this way, dark, dark brown or black hair can be lightened by 4 to 6 nuances in one step. Until applied, the hydrogen peroxide and the percarbonates or persalts are stored separately from one another so as not to deactivate the percarbonates or persalts prematurely. The hydrogen peroxide component, which comprises an aqueous solution of hydrogen peroxide, has an acid pH value, in particular a pH value of 2.5 to 5.5, and in particular of 3 to 5, each measured at 20° C., so as to stabilize the hydrogen peroxide.

For the melanin-decomposing action of hydrogen peroxide and the blonding action on the keratin fiber, however, it is advantageous if the application mixture made of hydrogen peroxide solution and persalt has an alkaline pH value, which is preferably in the range of 8 to 12, particularly preferably in the range of 8.5 to 11.5, and exceptionally preferably in the range of 9 to 10.5, each measured at 20° C.

There are several options for setting an alkaline pH value of the lightening application mixture:

In addition to the at least one persalt or percarbonate, the blonding powder contains at least one powdery alkalizing agent in a total amount such that the application mixture has the desired alkaline value; or the hydrogen peroxide solution is combined not only with the blonding powder, but additionally with an alkalizing agent preparation to yield the application mixture.

If oxidation dye precursors and/or direct dyes are added to the alkalizing agent preparation and/or the blonding powder, the hair can be dyed at the same time. Corresponding 3-component hair coloring agents are offered in particular for consumers having very dark hair rich in melanin.

Lightening, however, goes hand in hand with damage to the hair since not only the pigments of the hair, but also the structural components of the hair are oxidatively damaged. Depending on the degree of the damage, this may range from rough, brittle hair that is difficult to comb, through reduced resistance and ultimate tensile strength of the hair, to hair breakage. The greater the amount of hydrogen peroxide used, and optionally of the persalts or percarbonates, the more extensive is the damage generally caused to the keratin fibers.

So as to minimize damage to the hair and compensate for the damaging effect of the oxidizing agents, efforts are being consistently made to formulate persalt-containing hair lightening and coloring agents having a higher content of oils.

For example, blonding agent suspensions are described in the prior art, which represent anhydrous suspensions of fine-particled persalts or percarbonates that are solid at 25° C. and 1013 mbar in an oil, or an oil mixture, which may optionally be thickened using an oil gelling agent, see EP 0778020, EP 1034777, and EP 1380287. The disadvantage here is that it is difficult to produce a homogeneous mixture from this very hydrophobic paste and the highly hydrous hydrogen peroxide preparation, as well as optionally the typically likewise hydrous alkalizing agent preparation, requiring extended vigorous shaking or stirring. A blonding agent suspension is also more complex to produce in terms of the technique than a powdery persalt mixture.

It is therefore desirable to provide agents for lightening or blonding keratin fibers, and in particular human hair, that damage the keratin fibers as little as possible and that are easy to produce and handle. The reduction in the fiber damage is preferably not to be achieved by way of oils, but by alternative active nourishing agents. Furthermore, other desirable features and characteristics of the present invention will become apparent from the subsequent detailed description of the invention and the appended claims, taken in conjunction with this background of the invention.

BRIEF SUMMARY OF THE INVENTION

A first subject matter of the present invention is a blonding powder, including:
a) at least one oxidizing agent, selected from sodium percarbonates and inorganic salts of a peroxosulfuric acid, and mixtures thereof;
b) furthermore at least one dicarboxylic acid having 2 to 10 carbon atoms, selected from succinic acid, malic acid, oxalic acid, malonic acid, adipic acid, pimelic acid, suberic acid, azelaic acid, sebacic acid, maleic acid, fumaric acid, D-tartaric acid, L-tartaric acid, meso-tartaric acid, racemic acid, alpha-ketoglutaric acid, beta-ketoglutaric acid, oxaloacetic acid, and/or at least one salt of these acids, and mixtures of these compounds, wherein the dicarboxylic acid having 2 to 10 carbon atoms is preferably selected from succinic acid, malic acid, maleic acid, and the salts of succinic acid, malic acid and maleic acid;
c) furthermore at least one amino acid, selected from arginine, lysine, histidine or at least one of the salts of these amino acids; and
d) 0 to 8 wt. % water, based on the weight of the blonding powder.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

According to the invention, keratin-containing or keratin fibers shall be understood to mean furs, wool, feathers, and in particular human hair. Although the agents according to the invention are primarily suitable for blonding and/or lightening keratin-containing fibers, in principle there are no objections to using them in other fields as well.

One suitable parameter for quantifying the damage to the fibers, and in particular the damage to the hair, is the measurement of the tensile strength (Young's modulus) of the keratin fibers.

WO 2005115314A1 discloses a method for restructuring keratin fibers, in which the keratin fibers are brought in contact with cystine and at least one dicarboxylic acid having 2 to 10 carbon atoms, wherein preferred dicarboxylic acids are selected from oxalic acid, malonic acid, succinic acid, glutaric acid, adipic acid, pimelic acid, azelaic acid, maleic acid, fumaric acid, and sorbic acid, and succinic acid is particularly preferred. DE 10051774 A1 describes the use of short-chain carboxylic acids having a molecular weight below 750 g/mol in cosmetic agents as an active ingredient for restructuring keratin fibers. EP 1174112A discloses hair treatment agents that, in addition to an organic acid, comprise an organic solvent, a cationic surfactant, and a higher alcohol as further essential components, and that are used to repair pores formed inside hair.

According to the invention, the term "powder" or "powdery" shall be understood to mean a pourable form of administration that is solid at 20° C. and 1013 mbar and composed of individual particles, in which the individual particles have particle sizes in the range of 0.1 μm to no more than 1.6 mm. The particle sizes can preferably be determined by way of laser diffraction measurement according to ISO 13320-1 (2009). Optionally, the grain size of the particles can be adapted to the requirements with regard to the blonding powder by physical treatment such as sifting, pressing, granulating or pelletizing, or by adding certain auxiliary substances, for example so as to enable better miscibility of the individual powder components, or the miscibility of the blonding powder with a hydrogen peroxide preparation.

Preferred blonding powders according to the invention have a bulk density in the range of 500 to 1000 g/L (grams/liter), preferably 550 to 900 g/L, and particularly preferably 600 to 820 g/L. The bulk density is preferably determined according to EN ISO 600 DIN 53468.

Unless indicated otherwise, all temperature information refers to a pressure of 1013 mbar.

As a first essential component, the blonding powder according to the invention comprises at least one oxidizing agent, which is selected from sodium percarbonates and inorganic salts of a peroxosulfuric acid, and mixtures thereof.

Sodium percarbonates shall be understood to mean adducts of sodium carbonate and hydrogen peroxide. Commercially available sodium percarbonate has the average composition 2 $Na_2CO_3 \cdot 3H_2O_2$. Sodium percarbonate is present in the form of a white, water-soluble powder that decomposes easily to sodium carbonate and "active" oxygen exhibiting bleaching and oxidizing action.

Peroxosulfuric acids shall be understood to mean peroxodisulfuric acid and peroxomonosulfuric acid (Caro's acid).

The at least one inorganic salt of a peroxosulfuric acid is preferably selected from ammonium peroxodisulfate, alkali metal peroxodisulfates, ammonium peroxomonosulfate, alkali metal peroxomonosulfates and alkali metal hydrogenperoxomonosulfates. Particularly preferred are ammonium peroxodisulfate, potassium peroxodisulfate, sodium peroxodisulfate and potassium hydrogenperoxomonosulfate. Moreover, it has proven to be particularly preferred while conducting the work of the present invention for the blonding powder according to the invention to contain at least two different peroxodisulfates. Preferred peroxodisulfate salts are combinations of ammonium peroxodisulfate and potassium peroxodisulfate and/or sodium peroxodisulfate.

Preferred blonding powders according to the invention comprise at least one oxidizing agent, which is selected from sodium percarbonates and inorganic salts of a peroxosulfuric acid and mixtures thereof, in a total amount of 5 to 85 wt. %, preferably 10 to 75 wt. %, particularly preferably 15 to 65 wt. %, and exceptionally preferably 20 to 55 wt. %, each based on the weight of the blonding powder.

As a second essential component, the blonding powder according to the invention furthermore comprises at least one dicarboxylic acid having 2 to 10 carbon atoms, selected from succinic acid, malic acid, oxalic acid, malonic acid, adipic acid, pimelic acid, suberic acid, azelaic acid, sebacic acid, maleic acid, fumaric acid, D-tartaric acid, L-tartaric acid, meso-tartaric acid, racemic acid, alpha-ketoglutaric acid, beta-ketoglutaric acid, oxaloacetic acid, and/or at least one salt of these acids, and mixtures of these compounds, wherein the at least one dicarboxylic acid having 2 to 10 carbon atoms is preferably selected from succinic acid, malic acid, and maleic acid, and the salts thereof.

Suitable salts of dicarboxylic acids having 2 to 10 carbon atoms according to the invention are selected from the mono-salts and di-salts of the anions of succinic acid, malic acid, oxalic acid, malonic acid, adipic acid, pimelic acid, suberic acid, azelaic acid, sebacic acid, maleic acid, fumaric acid, D-tartaric acid, L-tartaric acid, meso-tartaric acid, racemic acid, alpha-ketoglutaric acid, beta-ketoglutaric acid and oxaloacetic acid with ammonium ions, alkali metal ions, alkaline earth metal ions and the ions of basic amino acids, such as arginine, lysine and histidine, and in particular with lithium, sodium, potassium, magnesium and calcium ions, and mixtures of these salts.

The particularly preferred succinic acid according to the invention has a melting point in the range of 185 to 187° C. at 1013 mbar, and is thus a solid at 20° C. Suitable salts of succinic acid according to the invention are selected from the succinates and hydrogen succinates of ammonium ions, alkali metal ions, alkaline earth metal ions and the ions of basic amino acids, such as arginine, lysine and histidine, and in particular the lithium, sodium, potassium, magnesium and calcium ions, or the succinates and hydrogen succinates of basic amino acids, such as arginine, lysine and/or histidine, such as arginine succinate, and mixtures of these salts. The aforementioned salts of succinic acid can also contain bound constitutional water, and in particular the sodium succinate hexahydrate, which is particularly preferred according to the invention.

The particularly preferred malic acid according to the invention is optically active. The racemic DL-malic acid has a melting point in the range of 131 to 132° C. at 1013 mbar, and is thus a solid at 20° C. The enantiomers D-malic acid and L-malic acid each have a melting point in the range of 100 to 101° C. at 1013 mbar. For cost reasons, the racemic DL-malic acid is preferred.

Suitable salts of malic acid according to the invention are selected from the malates and hydrogen malates of ammonium ions, alkali metal ions, alkaline earth metal ions and the ions of basic amino acids, such as arginine, lysine and histidine, and in particular of lithium, sodium, potassium, magnesium and calcium ions, and mixtures of these salts, and in particular disodium malate and dipotassium malate, but also calcium malate. The aforementioned suitable salts of malic acid according to the invention can contain bound constitutional water, and in particular the disodium malate hemihydrate and the disodium malate trihydrate.

The preferred oxalic acid according to the invention has a melting point of 189.5° C. (anhydrous) or, in the form of the dihydrate, a melting point of 101.5° C. at 1013 mbar. Suitable salts of oxalic acid according to the invention are selected from the oxalates and hydrogen oxalates of ammonium ions, alkali metal ions, alkaline earth metal ions and the ions of basic amino acids, such as arginine, lysine and histidine, and in particular of lithium, sodium, potassium, magnesium and calcium ions, and mixtures of these salts.

The preferred malonic acid according to the invention has a melting point of 135° C. at 1013 mbar. Suitable salts of malonic acid according to the invention are selected from the malates and hydrogen malates of ammonium ions, alkali metal ions, alkaline earth metal ions and the ions of basic amino acids, such as arginine, lysine and histidine, and in particular of lithium, sodium, potassium, magnesium and calcium ions, and mixtures of these salts.

The preferred adipic acid according to the invention has a melting point of 152° C. at 1013 mbar. Suitable salts of adipic acid according to the invention are selected from the adipates and hydrogen adipates of ammonium ions, alkali metal ions, alkaline earth metal ions and the ions of basic amino acids, such as arginine, lysine and histidine, and in particular of lithium, sodium, potassium, magnesium and calcium ions, and mixtures of these salts.

The preferred pimelic acid according to the invention has a melting point of 105° C. at 1013 mbar. Suitable salts of pimelic acid according to the invention are selected from the pimelates and hydrogen pimelates of ammonium ions, alkali metal ions, alkaline earth metal ions and the ions of basic amino acids, such as arginine, lysine and histidine, and in particular of lithium, sodium, potassium, magnesium and calcium ions, and mixtures of these salts.

The preferred suberic acid according to the invention has a melting point of 144° C. at 1013 mbar. Suitable salts of suberic acid according to the invention are selected from the suberates and hydrogen suberates of ammonium ions, alkali metal ions, alkaline earth metal ions and the ions of basic amino acids, such as arginine, lysine and histidine, and in particular of lithium, sodium, potassium, magnesium and calcium ions, and mixtures of these salts.

The preferred azelaic acid according to the invention has a melting point of 106° C. at 1013 mbar. Suitable salts of azelaic acid according to the invention are selected from the azelates and hydrogen azelates of ammonium ions, alkali metal ions, alkaline earth metal ions and the ions of basic amino acids, such as arginine, lysine and histidine, and in particular of lithium, sodium, potassium, magnesium and calcium ions, and mixtures of these salts.

The preferred sebacic acid according to the invention has a melting point of 134.5° C. at 1013 mbar. Suitable salts of sebacic acid according to the invention are selected from the sebacates and hydrogen sebacates of ammonium ions, alkali metal ions, alkaline earth metal ions and the ions of basic amino acids, such as arginine, lysine and histidine, and in particular of lithium, sodium, potassium, magnesium and calcium ions, and mixtures of these salts.

The particularly preferred maleic acid according to the invention has a melting point of 130 to 131° C. (made of ethanol or benzene) and of 138 to 139° C. (made of water) at 1013 mbar. Suitable salts of maleic acid according to the invention are selected from the maleates and hydrogen maleates of ammonium ions, alkali metal ions and alkaline earth metal ions, and in particular of lithium, sodium, potassium, magnesium and calcium ions, and mixtures of these salts.

The particularly preferred fumaric acid according to the invention has a melting point of 287° C. in a fused tube at 1013 mbar; fumaric acid sublimes at 200° C. Suitable salts of fumaric acid according to the invention are selected from the fumarates and hydrogen fumarates of ammonium ions, alkali metal ions and alkaline earth metal ions, and in particular of lithium, sodium, potassium, magnesium and calcium ions, and mixtures of these salts.

The particularly preferred D-tartaric acid (left-handed) according to the invention has a melting point of 168 to 170° C. at 1013 mbar. Suitable salts of D-tartaric acid according to the invention are selected from the tartrates and hydrogen tartrates of ammonium ions, alkali metal ions, and alkaline earth metal ions and in particular of lithium, sodium, potassium, magnesium and calcium ions, and mixtures of these salts.

The particularly preferred L-tartaric acid (right-handed) according to the invention has a melting point of 168 to 170° C. at 1013 mbar. Suitable salts of L-tartaric acid according to the invention are selected from the tartrates and hydrogen tartrates of ammonium ions, alkali metal ions, and alkaline earth metal ions and in particular of lithium, sodium, potassium, magnesium and calcium ions, and mixtures of these salts.

The particularly preferred meso-tartaric acid according to the invention has a melting point of 140° C. at 1013 mbar. Suitable salts of meso-tartaric acid according to the invention are selected from the tartrates and hydrogen tartrates of ammonium ions, alkali metal ions, and alkaline earth metal ions and in particular of lithium, sodium, potassium, magnesium and calcium ions, and mixtures of these salts.

The particularly preferred racemic acid according to the invention is the racemic mixture of D-tartaric acid and L-tartaric acid. Racemic acid has a melting point of 206° C. at 1013 mbar. Suitable salts of racemic acid according to the invention are selected from the tartrates and hydrogen tartrates of ammonium ions, alkali metal ions, and alkaline earth metal ions and in particular of lithium, sodium, potassium, magnesium and calcium ions, and mixtures of these salts.

The particularly preferred alpha-ketoglutaric acid according to the invention has a melting point of 112 to 116° C. at 1013 mbar. Suitable salts of alpha-ketoglutaric acid according to the invention are selected from the alpha-ketoglutarates and alpha-ketohydrogenglutarates of ammonium ions, alkali metal ions, and alkaline earth metal ions and in particular of lithium, sodium, potassium, magnesium and calcium ions, and mixtures of these salts.

The particularly preferred beta-ketoglutaric acid according to the invention has a melting point of 122° C. at 1013 mbar; it decomposes when melting. Suitable salts of beta-ketoglutaric acid according to the invention are selected from the beta-ketoglutarates and beta-ketohydrogenglutarates of ammonium ions, alkali metal ions and alkaline earth metal ions, and in particular of lithium, sodium, potassium, magnesium and calcium ions, and mixtures of these salts.

The particularly preferred oxaloacetic acid according to the invention has a melting point of 161° C. at 1013 mbar. Suitable salts of oxaloacetic acid according to the invention are selected from the oxaloacetates and oxalohydrogenacetates of ammonium ions, alkali metal ions, and alkaline earth metal ions and in particular of lithium, sodium, potassium, magnesium and calcium ions, and mixtures of these salts.

Preferred blonding powders according to the invention comprise the at least one dicarboxylic acid having 2 to 10 carbon atoms, selected from succinic acid, malic acid, oxalic acid, malonic acid, adipic acid, pimelic acid, suberic acid, azelaic acid, sebacic acid, and/or at least one salt of these acids, in a total amount, converted to the mass of free dicarboxylic acid, of 0.03 to 7 wt. %, preferably 0.1 to 5 wt. %, particularly preferably 0.5 to 3 wt. %, and exceptionally preferably 0.9 to 1.5 wt. %, each based on the weight of the blonding powder.

Further preferred blonding powders according to the invention comprise succinic acid and/or at least one salt of succinic acid in a total amount, converted to the mass of free dicarboxylic acid, of 0.03 to 7 wt. %, preferably 0.1 to 5 wt. %, particularly preferably 0.5 to 3 wt. %, and exceptionally preferably 0.9 to 1.5 wt. %, each based on the weight of the blonding powder.

Further preferred blonding powders according to the invention comprise malic acid and/or at least one salt of malic acid in a total amount, converted to the mass of free dicarboxylic acid, of 0.03 to 7 wt. %, preferably 0.1 to 5 wt. %, particularly preferably 0.5 to 3 wt. %, and exceptionally preferably 0.9 to 1.5 wt. %, each based on the weight of the blonding powder.

Further preferred blonding powders according to the invention comprise maleic acid and/or at least one salt of maleic acid in a total amount, converted to the mass of free dicarboxylic acid, of 0.03 to 7 wt. %, preferably 0.1 to 5 wt. %, particularly preferably 0.5 to 3 wt. %, and exceptionally preferably 0.9 to 1.5 wt. %, each based on the weight of the blonding powder.

Further preferred blonding powders according to the invention comprise fumaric acid and/or at least one salt of fumaric acid in a total amount, converted to the mass of free dicarboxylic acid, of 0.03 to 7 wt. %, preferably 0.1 to 5 wt. %, particularly preferably 0.5 to 3 wt. %, and exceptionally preferably 0.9 to 1.5 wt. %, each based on the weight of the blonding powder.

Further preferred blonding powders according to the invention comprise oxalic acid and/or at least one salt of oxalic acid in a total amount, converted to the mass of free dicarboxylic acid, of 0.03 to 7 wt. %, preferably 0.1 to 5 wt. %, particularly preferably 0.5 to 3 wt. %, and exceptionally preferably 0.9 to 1.5 wt. %, each based on the weight of the blonding powder.

Further preferred blonding powders according to the invention comprise malonic acid and/or at least one salt of malonic acid in a total amount, converted to the mass of free dicarboxylic acid, of 0.03 to 7 wt. %, preferably 0.1 to 5 wt. %, particularly preferably 0.5 to 3 wt. %, and exceptionally preferably 0.9 to 1.5 wt. %, each based on the weight of the blonding powder.

Further preferred blonding powders according to the invention comprise adipic acid and/or at least one salt of adipic acid in a total amount, converted to the mass of free dicarboxylic acid, of 0.03 to 7 wt. %, preferably 0.1 to 5 wt. %, particularly preferably 0.5 to 3 wt. %, and exceptionally preferably 0.9 to 1.5 wt. %, each based on the weight of the blonding powder.

Further preferred blonding powders according to the invention comprise pimelic acid and/or at least one salt of pimelic acid in a total amount, converted to the mass of free dicarboxylic acid, of 0.03 to 7 wt. %, preferably 0.1 to 5 wt. %, particularly preferably 0.5 to 3 wt. %, and exceptionally preferably 0.9 to 1.5 wt. %, each based on the weight of the blonding powder.

Further preferred blonding powders according to the invention comprise suberic acid and/or at least one salt of suberic acid in a total amount, converted to the mass of free dicarboxylic acid, of 0.03 to 7 wt. %, preferably 0.1 to 5 wt. %, particularly preferably 0.5 to 3 wt. %, and exceptionally preferably 0.9 to 1.5 wt. %, each based on the weight of the blonding powder.

Further preferred blonding powders according to the invention comprise azelaic acid and/or at least one salt of azelaic acid in a total amount, converted to the mass of free dicarboxylic acid, of 0.03 to 7 wt. %, preferably 0.1 to 5 wt. %, particularly preferably 0.5 to 3 wt. %, and exceptionally preferably 0.9 to 1.5 wt. %, each based on the weight of the blonding powder.

Further preferred blonding powders according to the invention comprise sebacic acid and/or at least one salt of sebacic acid in a total amount, converted to the mass of free dicarboxylic acid, of 0.03 to 7 wt. %, preferably 0.1 to 5 wt. %, particularly preferably 0.5 to 3 wt. %, and exceptionally preferably 0.9 to 1.5 wt. %, each based on the weight of the blonding powder.

Further preferred blonding powders according to the invention comprise D-tartaric acid and/or at least one salt of D-tartaric acid in a total amount, converted to the mass of free dicarboxylic acid, of 0.03 to 7 wt. %, preferably 0.1 to 5 wt. %, particularly preferably 0.5 to 3 wt. %, and exceptionally preferably 0.9 to 1.5 wt. %, each based on the weight of the blonding powder.

Further preferred blonding powders according to the invention comprise L-tartaric acid and/or at least one salt of L-tartaric acid in a total amount, converted to the mass of free dicarboxylic acid, of 0.03 to 7 wt. %, preferably 0.1 to 5 wt. %, particularly preferably 0.5 to 3 wt. %, and exceptionally preferably 0.9 to 1.5 wt. %, each based on the weight of the blonding powder.

Further preferred blonding powders according to the invention comprise meso-tartaric acid and/or at least one salt of meso-tartaric acid in a total amount, converted to the mass of free dicarboxylic acid, of 0.03 to 7 wt. %, preferably 0.1 to 5 wt. %, particularly preferably 0.5 to 3 wt. %, and exceptionally preferably 0.9 to 1.5 wt. %, each based on the weight of the blonding powder.

Further preferred blonding powders according to the invention comprise racemic acid and/or at least one salt of racemic acid in a total amount, converted to the mass of free dicarboxylic acid, of 0.03 to 7 wt. %, preferably 0.1 to 5 wt. %, particularly preferably 0.5 to 3 wt. %, and exceptionally preferably 0.9 to 1.5 wt. %, each based on the weight of the blonding powder.

Further preferred blonding powders according to the invention comprise alpha-ketoglutaric acid and/or at least one salt of alpha-ketoglutaric acid in a total amount, converted to the mass of free dicarboxylic acid, of 0.03 to 7 wt. %, preferably 0.1 to 5 wt. %, particularly preferably 0.5 to 3 wt. %, and exceptionally preferably 0.9 to 1.5 wt. %, each based on the weight of the blonding powder.

Further preferred blonding powders according to the invention comprise beta-ketoglutaric acid and/or at least one salt of beta-ketoglutaric acid in a total amount, converted to the mass of free dicarboxylic acid, of 0.03 to 7 wt. %, preferably 0.1 to 5 wt. %, particularly preferably 0.5 to 3 wt. %, and exceptionally preferably 0.9 to 1.5 wt. %, each based on the weight of the blonding powder.

Further preferred blonding powders according to the invention comprise oxaloacetic acid and/or at least one salt of oxaloacetic acid in a total amount, converted to the mass of free dicarboxylic acid, of 0.03 to 7 wt. %, preferably 0.1 to 5 wt. %, particularly preferably 0.5 to 3 wt. %, and exceptionally preferably 0.9 to 1.5 wt. %, each based on the weight of the blonding powder.

As a third essential component, the blonding powder according to the invention furthermore comprises at least one amino acid, selected from arginine, lysine, histidine or at least one of the salts of these amino acids. Mixtures of arginine and lysine are particularly preferred according to the invention. Among the salts of arginine, lysine or histidine that are preferably suited according to the invention are the ammonium salts, alkali metal salts and alkaline earth metal salts, and in particular the lithium, sodium, potassium, magnesium and calcium salts, moreover the hydrohalides, and in particular the hydrochlorides, moreover the salts with at least one above-described dicarboxylic acid having 2 to 10 carbon atoms, and mixtures of these salts. A particularly preferred amino acid salt according to the invention is lysine hydrochloride. The amino acids suited according to the invention, selected from arginine, lysine, histidine and the salts thereof, can also comprise constitutional water.

Preferred blonding powders according to the invention comprise at least one amino acid, selected from arginine, lysine, histidine or at least one salt of these amino acids, in a total amount, converted to the mass of free amino acid, of 0.1 to 7 wt. %, preferably 0.2 to 5 wt. %, particularly preferably 0.5 to 2.5 wt. %, and exceptionally preferably 1 to 2 wt. %, each based on the weight of the blonding powder.

The combination of succinic acid, lysine and arginine has been found to be exceptionally preferred according to the invention. The combination of succinic acid and arginine is likewise exceptionally preferred.

Particularly preferred blonding powders according to the invention comprise succinic acid and/or at least one succinic acid salt in a total amount, converted to the mass of free dicarboxylic acid, of 0.03 to 7 wt. %, preferably 0.05 to 5 wt. %, particularly preferably 0.1 to 3.0 wt. %, and exceptionally preferably 0.2 to 1.5 wt. %, each based on the weight of the blonding powder, and furthermore at least one amino acid, selected from arginine, lysine or at least one salt of these amino acids, in a total amount, converted to the mass of free amino acid, of 0.1 to 7 wt. %, preferably 0.2 to 5 wt. %, particularly preferably 0.5 to 2.5 wt. %, and exceptionally preferably 1 to 2 wt. %, each based on the weight of the blonding powder.

The combination of malic acid, lysine and arginine has furthermore been found to be exceptionally preferred according to the invention. The combination of malic acid and arginine is likewise exceptionally preferred.

Particularly preferred blonding powders according to the invention comprise malic acid and/or at least one malic acid salt in a total amount, converted to the mass of free dicarboxylic acid, of 0.03 to 7 wt. %, preferably 0.05 to 5 wt. %, particularly preferably 0.1 to 3.0 wt. %, and exceptionally preferably 0.2 to 1.5 wt. %, each based on the weight of the blonding powder, and furthermore at least one amino acid, selected from arginine, lysine, histidine or at least one salt of these amino acids, in a total amount, converted to the mass of free amino acid, of 0.1 to 7 wt. %, preferably 0.2 to 5 wt. %, particularly preferably 0.5 to 2.5 wt. %, and exceptionally preferably 1 to 2 wt. %, each based on the weight of the blonding powder.

The blonding powders according to the invention have a water content of 0 to 8 wt. %, preferably 0.1 to 4.5 wt. %, and particularly preferably 0.5 to 2.5 wt. %, each based on the weight of the blonding powder. This information refers to the content of free water. Not considered is the content of molecularly bound water or constitutional water that individual powder components may comprise.

The water content can be determined, for example, based on ISO 4317 (Version 2011-12) by way of Karl Fischer titration.

Preferred blonding powders according to the invention additionally comprise at least one inorganic alkalizing agent that is solid at 20° C. and 1013 mbar, which is preferably present in a total amount of 1 to 60 wt. %, preferably 5 to 55 wt. %, particularly preferably 10 to 50 wt. %, and exceptionally preferably 15 to 45 wt. %, each based on the weight of the blonding powder. Particularly preferred inorganic alkalizing agents according to the invention that are solid at 20° C. and 1013 mbar are selected from alkali metal silicates, alkaline earth metal silicates, alkaline earth metal hydroxide carbonates, alkaline earth metal carbonates, alkali metal metasilicates, alkaline earth metal metasilicates, alkali metal hydroxides, alkaline earth metal hydroxides, alkali metal and alkaline earth metal phosphates, and alkali metal and alkaline earth metal hydrogen phosphates, and mixtures of these substances. Particularly preferred inorganic alkalizing agents according to the invention that are solid at 20° C. and 1013 mbar are selected from sodium metasilicates having a molar $SiO_2/Na_2O$ ratio of $\geq 2$, and preferably 2.5 to 3.5, and from magnesium hydroxide carbonates, and mixtures of these substances. Preferred magnesium hydroxide carbonates according to the invention are those of formula $MgCO_3Mg(OH)_2 \cdot 2H_2O$ and those of formula $MgCO_3Mg(OH)_2$. Magnesium hydroxide carbonate of formula $MgCO_3Mg(OH)_2$ is particularly preferred according to the invention.

Particularly preferred blonding powders according to the invention contain, in each case based on the total weight thereof, 25 to 50 wt. %, preferably 30 to 45 wt. %, and particularly preferably 34 to 40 wt. % sodium silicates having a molar $SiO_2/Na_2O$ ratio of $\geq 2$, and preferably 2.5 to 3.5, and 2 to 20 wt. %, preferably 5 to 15 wt. %, and particularly preferably 8 to 25 wt. % magnesium hydroxide carbonate as inorganic alkalizing agents that are solid at 20° C. and 1013 mbar.

Exceptionally preferred blonding powders according to the invention contain, in each case based on the total weight thereof, 25 to 50 wt. %, preferably 30 to 45 wt. %, and particularly preferably 34 to 40 wt. % sodium silicates having a molar $SiO_2/Na_2O$ ratio of $\geq 2$, and preferably 2.5 to 3.5, and 2 to 20 wt. %, preferably 5 to 15 wt. %, and particularly preferably 10 to 13 wt. % magnesium hydroxide carbonate of formula $MgCO_3.Mg(OH)_2$ as inorganic alkalizing agents that are solid at 20° C. and 1013 mbar.

If the blonding powder according to the invention, or the preferred blonding powder according to the invention, comprises one or more inorganic carbonates, be it as an alkalizing agent or as an oxidizing agent in the form of adducts of sodium carbonate and hydrogen peroxide, the content thereof is preferably selected such that the molar $CO_3^2$ total concentration in the application mixture having the oxidation composition (Ox) described below is at least 0.015 mol/100 grams of application mixture.

If the blonding powder according to the invention, or the preferred blonding powder according to the invention, comprises one or more inorganic carbonates, be it as an alkalizing agent or as an oxidizing agent in the form of adducts of sodium carbonate and hydrogen peroxide, the content thereof is particularly preferably selected such that the molar $CO_3^{2-}$ total concentration in the application mixture having the oxidation composition (Ox) described below is calculated to be at least four times greater than the total concentration of proton donors.

If the blonding powder according to the invention, or the preferred blonding powder according to the invention, comprises one or more inorganic carbonates, be it as an alkalizing agent or as an oxidizing agent in the form of adducts of sodium carbonate and hydrogen peroxide, the content thereof is exceptionally preferably selected such that the molar $CO_3^{2-}$ total concentration in the application mixture having the oxidation composition (Ox) described below is at least 0.015 mol/100 grams of application mixture and is calculated to be at least four times higher than the total concentration of proton donors.

For anti-dusting of the blonding powder according to the invention, it is possible to add at least one anti-dusting agent, which is in particular selected from at least one oil, and in particular selected from paraffin oil, silicone oil or ester oil, and mixtures of these oils.

Preferred blonding powders according to the invention thus additionally comprise at least one oil in a total amount of 0.1 to 15 wt. %, preferably 0.5 to 10 wt. %, particularly preferably 1 to 8 wt. %, and exceptionally preferably 2 to 6 wt. %, each based on the weight of the blonding powder.

Preferred oils according to the invention are selected from natural and synthetic hydrocarbons, particularly preferably from paraffin oils, $C_{18}$ to $C_{30}$ isoparaffins, and in particular isoeicosane, polyisobutenes and polydecenes, furthermore selected from $C_8$ to $C_{16}$ isoparaffins, and in particular from isodecane, isododecane, isotetradecane and isohexadecane, and mixtures thereof, and 1,3-bis(2-ethylhexyl)cyclohexane.

Further preferred oils according to the invention are selected from the benzoic acid esters of linear or branched C8-22 alkanols. Particularly preferred are benzoic acid-C12-C15-alkyl esters Further preferred oils according to the invention are selected from fatty alcohols having 6 to 30 carbon atoms, which are unsaturated, or branched and saturated, or branched and unsaturated. Preferred alcohol oils are 2-hexyldecanol, 2-octyldodecanol, 2-ethylhexyl alcohol and isostearyl alcohol.

Further preferred cosmetic oils according to the invention are selected from the triglycerides (=triple esters of glycerol) of linear or branched, saturated or unsaturated, optionally hydroxylated C8-30 fatty acids. The use of natural oils can be particularly preferred, such as amaranth seed oil, apricot kernel oil, argan oil, avocado oil, babassu oil, cottonseed oil, borage seed oil, camelina oil, thistle oil, peanut oil, pomegranate seed oil, grapefruit seed oil, hemp oil, hazelnut oil, elderberry seed oil, currant seed oil, jojoba oil, linseed oil, macadamia nut oil, corn oil, almond oil, marula oil, evening primrose oil, olive oil, palm oil, palm kernel oil, Brazil nut oil, pecan nut oil, peach kernel oil, rapeseed oil, castor oil, sea buckthorn pulp oil, sea buckthorn kernel oil, sesame oil, soy bean oil, sunflower oil, grape seed oil, walnut oil, wild rose oil, wheat germ oil, and the liquid components of coconut oil, and the like. However, synthetic triglyceride oils, and in particular capric/caprylic triglycerides, are also preferred.

Further particularly preferred cosmetic oils according to the invention are selected from the dicarboxylic acid esters of linear or branched $C_2$ to $C_{10}$ alkanols, in particular diisopropyl adipate, di-n-butyl adipate, di-(2-ethylhexyl) adipate, dioctyl adipate, diethyl-/di-n-butyl/dioctyl sebacate, diisopropyl sebacate, dioctyl malate, dioctyl maleate, dicaprylyl maleate, diisooctyl succinate, di-2-ethylhexyl succinate, and di-(2-hexyldecyl) succinate.

Further particularly preferred cosmetic oils according to the invention are selected from among the esters of the linear or branched, saturated or unsaturated fatty alcohols having 2 to 30 carbon atoms with linear or branched, saturated or unsaturated fatty acids having 2 to 30 carbon atoms, which can be hydroxylated. These preferably include 2-hexyldecyl stearate, 2-hexyldecyl laurate, isodecyl neopentanoate, isononyl isononanoate, 2-ethylhexyl palmitate and 2-ethylhexyl stearate, isopropyl myristate, isopropyl palmitate, isopropyl stearate, isopropyl isostearate, isopropyl oleate, isooctyl stearate, isononyl stearate, isocetyl stearate, isononyl isononanoate, isotridecyl isononanoate, cetearyl isononanoate, 2-ethylhexyl laurate, 2-ethylhexyl isostearate, 2-ethylhexyl cocoate, 2-octyldodecyl palmitate, butyloctanoic acid-2-butyl octanoate, diisotridecyl acetate, n-butyl stearate, n-hexyl laurate, n-decyl oleate, oleyl oleate, oleyl erucate, erucyl oleate, erucyl erucate, ethylene glycol dioleate, and ethylene glycol dipalmitate.

Further preferred cosmetics oils according to the invention are selected from the addition products of 1 to 5 propylene oxide units to monohydric or polyhydric $C_{8-22}$-alkanols, such as octanol, decanol, decandiol, lauryl alcohol, myristyl alcohol, and stearyl alcohol, such as PPG-2 myristyl ether and PPG-3 myristyl ether. Further preferred cosmetic oils according to the invention are selected from the addition products of at least 6 ethylene oxide units and/or propylene oxide units to monohydric or polyhydric $C_{3-22}$ alkanols, such as glycerol, butanol, butanediol, myristyl alcohol and stearyl alcohol, which may optionally be esterified, such as PPG-14 butyl ether, PPG-9 butyl ether, PPG-10 butanediol, PPG-15 stearyl ether, and glycereth-7-diisononanoate.

Further preferred cosmetic oils according to the invention are selected from the $C_8$ to $C_{22}$ fatty alcohol esters of monovalent or polyvalent $C_2$ to $C_7$ hydroxycarboxylic acids, in particular the esters of glycolic acid, lactic acid, malic acid, tartaric acid, citric acid, and salicylic acid, such as $C_{12}$ to $C_{15}$ alkyl lactate.

Further preferred cosmetic oils according to the invention are selected from the symmetric, asymmetric or cyclic esters of carbonic acid with $C_{3-22}$ alkanols, $C_{3-22}$ alkane diols or $C_{3-22}$ alkane triols, such as dicaprylyl carbonate, or the esters according to DE 19756454 A1, and in particular glycerol carbonate.

Further cosmetic oils that are suitable according to the invention are selected from silicone oils, which also include, for example, dialkyl and alkyaryl siloxanes, such as decamethyl cyclopentasiloxane, dodecamethyl cyclohexasiloxane, dimethylpolysiloxane and methylphenylpolysiloxane, but also hexamethyldisiloxane, octamethyltrisiloxane and decamethyltetrasiloxane.

It may be exceptionally preferred according to the invention to use mixtures of the aforementioned oils.

Preferred blonding powders according to the invention are characterized in that the cosmetic oil is selected from natural and synthetic hydrocarbons, and particularly preferably from paraffin oils, C18 to $C_{30}$ isoparaffins, in particular isoeicosane, polyisobutenes and polydecenes, $C_8$ to $C_{16}$ isoparaffins, and 1,3-bis(2-ethylhexyl)cyclohexane; the benzoic acid esters of linear or branched $C_{8-22}$ alkanols; fatty alcohols having 6 to 30 carbon atoms, which are unsaturated, or branched and saturated, or branched and unsaturated; triglycerides of linear or branched, saturated or unsaturated, optionally hydroxylated $C_8$ to $C_{30}$ fatty acids, and in particular natural oils; the dicarboxylic acid esters of linear or branched $C_2$ to $C_{10}$ alkanols, the esters of linear or branched saturated or unsaturated fatty alcohols having 2 to 30 carbon atoms with linear or branched saturated or unsaturated fatty acids having 2 to 30 carbon atoms, which may be hydroxylated; the addition products of 1 to 5 propylene oxide units to monohydric or polyhydric $C_{8-22}$ alkanols; the addition products of at least 6 ethylene oxide and/or propylene oxide units to monohydric or polyhydric $C_{3-22}$ alkanols; the $C_8$ to $C_{22}$ fatty alcohol esters of monovalent or polyvalent $C_2$ to $C_7$ hydroxycarboxylic acids; the symmetric, asymmetric or cyclic esters of carbonic acid with $C_{3-22}$ alkanols, $C_{3-22}$ alkane diols or $C_{3-22}$ alkane triols; the esters of dimers of unsaturated $C_{12}$- to $C_{22}$ fatty acids (dimeric fatty acids) with monohydric linear, branched or cyclic $C_2$ to $C_{18}$ alkanols or with polyhydric linear or branched $C_2$ to $C_6$ alkanols; silicone oils and mixtures of the aforementioned substances, and preferably is present in a total amount of 0.1 to 15 wt. %, preferably 0.5 to 10 wt. %, particularly preferably 1 to 8 wt. %, and exceptionally preferably 2 to 6 wt. %, each based on the weight of the blonding powder.

Further preferred blonding agents according to the invention comprise at least one complexing agent, preferably in a total amount of 0.1 to 3 wt. %, preferably 0.2 to 2.5 wt. %, particularly preferably 0.5 to 2 wt. %, and exceptionally preferably 1 to 1.7 wt. %, each based on the weight of the blonding powder, wherein the at least one complexing agent particularly preferably is selected from the following acids and/or the alkali metal salts: ethylenediaminetetraacetic acid (EDTA); N-hydroxyethyl ethylenediaminetriacetic acid; aminotrimethylene phosphonic acid; diethylenetriaminepentaacetic acid; lauroyl ethylenediaminetriacetic acid; nitrilotriacetic acid; iminodisuccinic acid; N-2-hydroxyethyl iminodiacetic acid; ethylene glycol-bis-(beta-aminoethyl ether)-N,N-tetraacetic acid; aminotrimethylene phosphonic acid, pentasodium aminotrimethylene phosphonate, and mixtures thereof.

Further preferred blonding powders according to the invention comprise at least one polymer, which is selected from acrylic acid homopolymers and copolymers, methacrylic acid homopolymers and copolymers, itaconic acid homopolymers and copolymers, polysaccharides, which may be chemically and/or physically modified, and mixtures of these polymers, wherein particularly preferably one or more of the aforementioned polymers is present in a total amount of 0.1 to 6 wt. %, preferably 0.5 to 4 wt. %, particularly preferably 1 to 3.5 wt. %, and exceptionally preferably 2 to 3 wt. %, each based on the weight of the blonding powder.

A further subject matter of the present invention is a method for lightening keratin fibers, and in particular human hair, in which a blonding powder according to the invention, or a preferred blonding powder according to the invention, is mixed with an oxidation composition, which, in each case based on the weight thereof, contains 50 to 96 wt. %, preferably 70 to 93 wt. %, and particularly preferably 80 to 90 wt. % water, and 0.5 to 20 wt. % hydrogen peroxide, and furthermore comprises at least one pH setting agent in an amount such that the oxidation composition has a pH value in the range of 2.5 to 5.5, measured at 20° C., immediately thereafter is applied to the keratin fibers, left on the fibers for 5 to 60 minutes, and subsequently the fibers are rinsed with water, and optionally washed with a surfactant-containing cleansing agent, wherein the blonding powder (B) and the oxidation composition (Ox) are preferably mixed with each other in a weight-based ratio (B):(Ox) of 0.2 to 1, particularly preferably 0.3 to 0.8, more preferably 0.4 to 0.7, and exceptionally preferably 0.5 to 0.6.

The oxidation composition (Ox) used in the lightening method according to the invention essentially contains water and hydrogen peroxide. The concentration of the hydrogen peroxide is determined by legal requirements on the one hand, and by the desired effect on the other hand. It is 0.5 to 20 wt. %, preferably 3 to 12 wt. %, and particularly preferably 6 to 9 wt. % hydrogen peroxide (calculated as 100% $H_2O_2$), each based on the weight of the oxidation composition (Ox).

So as to stabilize the hydrogen peroxide, the oxidation composition (Ox) preferably has an acid pH value, and in particular a pH value in the range of 2.5 to 5.5, measured at 20° C. Furthermore complexing agents, preservatives and/or buffer substances are also present so as to stabilize the hydrogen peroxide.

According to the invention, the blonding powder is preferably composed such that the mixture with the aforementioned oxidation composition (Ox), which is to say the ready-to-use color changing agent, and in particular the blonding agent, has an alkaline pH value, preferably a pH value of 8 to 11.5, particularly preferably a pH value of 8.5 to 11, and exceptionally preferably a pH value of 9.0 to 10.5, each measured at 20° C.

Oxidation compositions (Ox) that are particularly preferably used according to the invention furthermore comprise at least one oil and/or at least one fat component having a melting point in the range of 23 to 110° C., preferably in a total amount of 0.1 to 60 wt. %, particularly preferably 0.5 to 40 wt. %, and exceptionally preferably 2 to 24 wt. %, each based on the weight of the oxidation composition (Ox) preferably used according to the invention. The oils suitable for the oxidation compositions (Ox) preferably used according to the invention are the same oils disclosed above as suitable anti-dusting agents.

Fat components that are preferably used according to the invention in the oxidation compositions (Ox) and have a melting point in the range of 23 to 110° C. are selected from linear saturated 1-alkanols having 12 to 30 carbon atoms, preferably in a total amount of 0.1 to 8 wt. %, and particularly preferably 3.0 to 6.0 wt. %, each based on the weight of the oxidation composition (Ox) used according to the invention.

The at least one linear saturated 1-alkanol having 12 to 30 carbon atoms is preferably selected from lauryl alcohol, myristyl alcohol, cetyl alcohol, stearyl alcohol, arachidyl alcohol and behenyl alcohol, and mixtures of these 1-alkanols, particularly preferably of cetyl alcohol, stearyl alcohol and cetyl alcohol/stearyl alcohol mixtures.

Oxidation compositions (Ox) preferably used according to the invention furthermore comprise, each based on the weight thereof, at least one linear saturated 1-alkanol having 12 to 30 carbon atoms in a total amount of 0.1 to 8 wt. %, and preferably in a total amount of 2 to 6 wt. %, wherein at least one 1-alkanol, selected from cetyl alcohol, stearyl alcohol and cetyl alcohol/stearyl alcohol mixtures, is present.

Further oxidation compositions (Ox) preferably used according to the invention comprise at least one fat component having a melting point in the range of 23 to 110° C., which is selected from esters of a saturated, monohydric $C_{16}$ to $C_{60}$ alkanol and a saturated $C_8$ to $C_{36}$ monocarboxylic acid, in particular cetyl behenate, stearyl behenate and $C_{20}$ to $C_{40}$ alkyl stearate, glycerol triesters of saturated linear $C_{12}$ to $C_{30}$ carboxylic acids, which may be hydroxylated, candelilla wax, carnauba wax, beeswax, saturated linear $C_{14}$ to $C_{36}$ carboxylic acids, and mixtures of the aforementioned substances.

Further oxidation compositions (Ox) preferably used according to the invention comprise at least one surfactant or at least one emulsifier, preferably in a total amount of 0.5 to 10 wt. %, and preferably 1 to 5 wt. %, each based on the weight of the oxidation composition (Ox) used according to the invention.

Surfactants and emulsifiers within the meaning of the present invention are amphiphilic (bifunctional) compounds, which are composed of at least one hydrophobic molecule part and at least one hydrophilic molecule part. The hydrophobic group is preferably a hydrocarbon chain having 8 to 28 carbon atoms, which can be saturated or unsaturated, linear or branched. This $C_8$ to $C_{28}$ alkyl chain is particularly preferably linear. Basic properties of the surfactants and emulsifiers are the oriented absorption at interfaces, the aggregation into micelles, and the formation of lyotropic phases.

According to the invention, anionic, non-ionic and cationic surfactants are particularly suitable. However, zwitterionic and amphoteric surfactants are also very well suited according to the invention.

All anionic surface-active substances that are suitable for use on the human body are suitable anionic surfactants in the compositions according to the invention. These are characterized by a water-soluble-rendering anionic group, such as a carboxylate, sulfate, sulfonate or phosphate group and a lipophilic alkyl group having 8 to 30 carbon atoms. In addition, glycol or polyglycol ether groups, ester, ether and amide groups and hydroxyl groups can be present in the molecule. Examples of suitable anionic surfactants are linear and branched fatty acids having 8 to 30 carbon atoms (soaps), alkyl ether carboxylic acids, acyl sarcosides, acyl taurides, acyl isothionates, sulfosuccinic acid monoalkyl and dialkyl esters, and sulfosuccinic acid monoalkyl polyoxyethyl esters, linear alkane sulfonates, linear alpha-olefin sulfonates, alkyl sulfates and alkyl ether sulfates, and alkyl and/or alkenyl phosphates. Preferred anionic surfactants are alkyl sulfates, alkyl ether sulfates and alkyl ether carboxylic acid salts, each having 10 to 18 carbon atoms, and preferably 12 to 14 carbon atoms, in the alkyl group, and up to 12 glycol ether groups, and preferably 2 to 6 glycol ether groups, in the molecule. Examples of such surfactants are the compounds having the INCI names Sodium Laureth Sulfate, Sodium Lauryl Sulfate, Sodium Myreth Sulfate or Sodium Laureth Carboxylate.

Zwitterionic surfactants are those surface-active compounds that carry at least one quaternary ammonium group and at least one carboxylate, sulfonate or sulfate group in the molecule. Particularly suited zwitterionic surfactants are those known as betaines, such as N-alkyl-N,N-dimethylammonium glycinates, for example coconut alkyl dimethylammonium glycinate, N-acylaminopropyl-N,N-dimethylammonium glycinate, for example, coconut acylaminopropyl dimethylammonium glycinate, and 2-alkyl-3-carboxymethyl-3-hydroxyethyl imidazolines, each having 8 to 18 carbon atoms in the alkyl or acyl group, and coconut acylamino ethylhydroxyethyl carboxymethyl glycinate. A preferred zwitterionic surfactant is the fatty acid amide derivative known by the INCI name Cocamidopropyl Betaine.

Amphoteric surfactants shall be understood to mean surface-active compounds that, in addition to a $C_8$ to $C_{24}$ alkyl or acyl group, contain at least one free amino group and at least one —COOH or —SO$_3$H group in the molecule, and that are capable of forming inner salts. Examples of suitable amphoteric surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids, and alkylaminoacetic acids, each having 8 to 24 carbon atoms in the alkyl group. Particularly preferred amphoteric surfactants are N-cocoalkylaminopropionate, cocoacylaminoethyl aminopropionate and $C_{12}$ to $C_{18}$ acyl sarcosine.

Non-ionic surfactants include a polyol group, a polyalkylene glycol ether group or a combination of a polyol and polyglycol ether group, for example, as the hydrophilic group. Such compounds include, for example, addition products of 4 to 50 moles ethylene oxide and/or 0 to 5 moles propylene oxide to linear and branched fatty alcohols, to fatty acids and to alkyl phenols, each having 8 to 20 carbon atoms in the alkyl group, ethoxylated mono-, di- and triglycerides, such as glycerol monolaurate+20 ethylene oxide, and glycerol monostearate+20 ethylene oxide, sorbitan fatty acid esters and addition products of ethylene oxide to sorbitan fatty acid esters, such as the polysorbates (Tween 20, Tween 21, Tween 60, Tween 61, Tween 81), addition products of ethylene oxide to fatty acid alkanolamides and fatty amines, and alkyl polyglycosides. Suitable non-ionic surfactants include in particular $C_8$ to $C_{22}$ alkyl monoglycosides and oligoglycosides and the ethoxylated analogs thereof, and ethylene oxide addition products to saturated or unsaturated linear fatty alcohols, each having 2 to 30 moles ethylene oxide per mole fatty alcohol.

Further oxidation compositions preferably used according to the invention are characterized in that the at least one anionic surfactant is selected from alkyl sulfates, alkyl ether sulfates and alkyl ether carboxylic acids, each having 10 to 18 carbon atoms, and preferably 12 to 14 carbon atoms, in the alkyl group, and up to 12 glycol ether groups, and preferably 2 to 6 glycol ether groups, in the molecule.

Further oxidation compositions preferably used according to the invention are characterized in that at least one nonanionic surfactant, selected from ethylene oxide addition products to saturated or unsaturated linear fatty alcohols with 2 to 30 moles ethylene oxide per mole fatty alcohol, respectively, and at least one anionic surfactant, selected from alkyl sulfates, alkyl ether sulfates and alkyl ether carboxylic acids, each having 10 to 18 carbon atoms, and preferably 12 to 14 carbon atoms, in the alkyl group, and up to 12 glycol ether groups, and preferably 2 to 6 glycol ether groups, in the molecule are present, wherein particularly preferably the weight ratio of the collectivity of all anionic surfactants to the collectivity of all non-ionic surfactants is in the range of 5 to 50, and preferably 10 to 30.

In principle, all cationic surface-active substances that are suitable for use on the human body are suitable cationic surfactants in the oxidation compositions (Ox) preferably used according to the invention. These are characterized by at least one water-soluble-rendering cationic group, such as a quaternary ammonium group, or by at least one water-soluble-rendering cationizable group, such as an amine group, and furthermore at least one (lipophilically acting) alkyl group having 6 to 30 carbon atoms or at least one (lipophilically acting) imidazole group or at least one (lipophilically acting) imidazylalkyl group.

Oxidation compositions (Ox) particularly preferably used according to the invention comprise at least one cationic surfactant, which is preferably selected from quaternary ammonium compounds having at least one C8 to C24 alkyl group, esterquats and amidoamines, each having at least one C8 to C24 acyl group, and mixtures thereof. Preferred quaternary ammonium compounds having at least one C8 to C24 alkyl group are ammonium halides, in particular chlorides and ammonium alkyl sulfates, such as methosulfates or ethosulfates, such as C8 to C24 alkyl trimethylammonium chlorides, C8 to C24 dialkyldimethylammonium chlorides and C8 to C24 trialkylmethylammonium chlorides, such as cetyl trimethylammonium chloride, stearyl trimethylammonium chloride, distearyl dimethylammonium chloride, lauryl dimethylammonium chloride, lauryl dimethyl benzylammonium chloride and tricetyl methylammonium chloride, and the imidazolium compounds known by the INCI names Quaternium-27, Quaternium-83, Quaternium-87 and Quaternium-91. The alkyl chains of the above-mentioned surfactants preferably comprise 8 to 24 carbon atoms.

The esterquats are cationic surfactants, which have both at least one ester function and at least one quaternary ammonium groups as structural elements, and furthermore at least one C8 to C24 alkyl group or C8 to C24 acyl group. Preferred esterquats are quaternized ester salts of fatty acids with triethanolamine, quaternized ester salts of fatty acids with diethanol alkylamines, and quaternized ester salts of fatty acids with 1,2-dihydroxypropyl dialkylamines. Such products are sold, for example, under the trademarks Stepantex®, Dehyquart® and Armocare®. N,N-bis(2-palmitoyloxyethyl)dimethylammonium chloride, distearoylethyl dimonium methosulfate, and distearoylethyl hydroxyethylmonium methosulfate are preferred examples of such esterquats.

The alkylamidoamines are usually produced by the amidation of natural or synthetic C8 to C24 fatty acids and fatty acid cuts with di(C1-C3)alkylaminoamines. A compound that is particularly suited according to the invention from this substance group is stearamidopropyl dimethylamine.

Oxidation compositions (Ox) used particularly preferably according to the invention include at least one cationic surfactant in a total amount of 0.01 to 5 wt. %, preferably 0.1 to 3 wt. %, and particularly preferably 0.3 to 2 wt. %, in each case based on the weight of oxidation composition (Ox) used according to the invention.

A further subject matter of the present invention is a multi-component packaging unit (kit of parts) for lightening keratin fibers, comprising at least two components that are packaged separately from each other, and characterized in that
i) the first component (I) is a blonding powder according to the invention, or a preferred blonding powder according to the invention;
ii) the second component (II) is an oxidation composition that, in each case based on the weight thereof, comprises 50 to 96 wt. %, preferably 70 to 93 wt. %, and particularly preferably 80 to 90 wt. % water, and 0.5 to 20 wt. % hydrogen peroxide, and has a pH value in the range of 2.5 to 5.5, measured at 20° C.;
wherein components (I) and (II) are preferably present in a weight-based ratio (I):(II) of 0.2 to 1, particularly preferably 0.3 to 0.8, more preferably 0.4 to 0.7, and exceptionally preferably 0.5 to 0.6.

A further subject matter of the present invention is a multi-component packaging unit (kit of parts) for changing the color of keratin fibers, and in particular of human hair, comprising at least three components that are packaged separately from each other, characterized in that
i) the first component (I) is a blonding powder according to the invention, or a preferred blonding powder according to the invention;
ii) the second component (II) is an oxidation composition that, in each case based on the weight thereof, comprises 50 to 96 wt. %, preferably 70 to 93 wt. %, and particularly preferably 80 to 90 wt. % water, and 0.5 to 20 wt. % hydrogen peroxide, and has a pH value in the range of 2.5 to 5.5, measured at 20° C.;
iii) the third component (III) is an alkalizing composition (Alk), which comprises water and at least one alkalizing agent, selected from ammonia, alkanolamines and mixtures thereof, and has a pH value in the range of 8 to 12, preferably 9 to 11, and particularly preferably 9.5 to 10.5, each measured at 20° C.,
wherein the blonding powder (B), the oxidation composition (Ox) and the alkalizing composition (Alk) are preferably present in a weight-based ratio (B):(Ox):(Alk) of (0.7 to 1.3):(2 to 3):(2 to 3), particularly preferably (0.8 to 1.2):(2.3 to 2.7):(2.3 to 2.7), and exceptionally preferably 1:2:2 to each other.

A multi-component packaging unit comprises multiple individual components, which are formulated separately from one another, and a shared packaging for these components, for example a folding box. The respective components are provided therein separately in different containers. A container within the scope of the present invention shall be understood to mean an enclosure present in the form of an optionally re-closable bottle, a tube, a can, an envelope, a sachet or a similar enclosure. There are no limits according to the invention as to the material of the enclosure. Preferably, however, these are enclosures made of glass or plastic material.

The packaging unit can moreover comprise application aids, such as combs or brushes, personal protective clothing, in particular disposable gloves, and usage instructions.

In a further preferred embodiment of the invention, a blonding powder according to the invention, or a preferred blonding powder according to the invention, can be combined with an alkalizing composition and with an oxidation composition to yield a lightening color changing agent for keratin fibers.

Since melanin, the pigment that gives fibers their colors, is destroyed to a certain degree when keratin fibers, and in particular hair, is treated with oxidizing agents, and in particular with hydrogen peroxide, the fibers/hair is/are automatically lightened, which is to say change or changes color even without the presence of a dye. The expression "changing the color" within the meaning of the present invention thus comprises both lightening and coloring using one or more dyes.

The alkalizing composition (Alk) used according to the invention contains water and at least one alkalizing agent, which is selected from ammonia, alkanolamines and mixtures thereof, and has a pH value in the range of 8 to 12, preferably 9 to 11, and particularly preferably 9.5 to 10.5, each measured at 20° C. Preferred alkanolamines are selected from monoethanolamine, 2-amino-2-methylpropanol and triethanolamine, and mixtures thereof, wherein monoethanolamine is particularly preferred. Ammonia is an exceptionally preferred alkalizing agent.

Ammonia ($NH_3$) is typically used in the form of the aqueous solution thereof. Aqueous ammonia solutions often contain ammonia ($NH_3$) in concentrations of 10 to 32 wt. %. The use of an aqueous ammonia solution comprising 25 wt. % ammonia ($NH_3$) is preferred.

In addition to ammonia and alkanolamines, at least one further alkalizing agent can be present, which is selected from alkali metal silicates, alkaline earth metal silicates, alkaline earth metal hydroxide carbonates, alkaline earth metal carbonates, alkali metal metasilicates, alkaline earth metal metasilicates, alkali metal hydroxides and alkaline earth metal hydroxides, and mixtures of these substances.

Preferably, ammonia and/or monoethanolamine are present in the alkalizing compositions that are preferably used according to the invention in amounts of 0.01 to 10 wt. %, preferably 0.1 to 7.5 wt. %, more preferably 0.5 to 5.5 wt. %, and particularly preferably 1.5 to 4.5 wt. %, each based on the weight of the alkalizing composition.

A further subject matter of the present invention is a method for changing the color of keratin fibers, and in particular human hair, in which a blonding powder according to the invention, or a preferred blonding powder according to the invention, is mixed with an oxidation composition (Ox), which, in each case based on the weight thereof, contains 50 to 96 wt. %, preferably 70 to 93 wt. %, and particularly preferably 80 to 90 wt. % water, and 0.5 to 20 wt. % hydrogen peroxide, and furthermore comprises at least one pH setting agent in an amount such that the oxidation composition has a pH value in the range of 2.5 to 5.5, measured at 20° C., and additionally with an alkalizing composition (Alk), which comprises water and at least one alkalizing agent, selected from ammonia, alkanolamines and mixtures thereof, and has a pH value in the range of 8 to 12, preferably 9 to 11, and particularly preferably 9.5 to 10.5, each measured at 20° C., immediately thereafter is applied to the keratin-containing fibers, left on the fibers for 5 to 60 minutes, and subsequently the fibers are rinsed with water, and optionally washed with a surfactant-containing cleansing agent, wherein the blonding powder (B), the oxidation composition (Ox) and the alkalizing composition (Alk) are preferably mixed with each other in a weight-based ratio (B):(Ox):(Alk) of (0.7 to 1.3):(2 to 3):(2 to 3), particularly preferably (0.8 to 1.2):(2.3 to 2.7):(2.3 to 2.7), and exceptionally preferably 1:2:2.

According to the invention, the blonding powder is preferably composed such that the mixture with the aforementioned oxidation composition (Ox) and with the aforementioned alkalizing composition (Alk), which is to say the ready-to-use color changing agent, and in particular the blonding agent, has an alkaline pH value, preferably a pH value of 8 to 11.5, particularly preferably a pH value of 8.5 to 11, and exceptionally preferably a pH value of 9.0 to 10.5, each measured at 20° C.

The ready-to use mixtures of a blonding powder according to the invention, or a preferred blonding powder according to the invention, with one of the aforementioned oxidation compositions (Ox), and optionally with one of the aforementioned alkalizing compositions (Alk), preferably have a viscosity in the range of 15,000 to 100,000 mPas, and particularly preferably 20,000 to 85,000 Pas, each measured at 20° C. using a Brookfield type DV-II+ viscometer, spindle 5 at a speed of 4 revolutions/minute. A viscosity in this range allows the ready-to-use agent to be easily applied, while having a flow behavior that ensures a sufficiently long residence time at the site of action on the keratin fibers for the agent.

So as to facilitate miscibility of the alkalizing composition used according to the invention with the blonding agent according to the invention, or the preferred blonding powder according to the invention, and the oxidation composition used according to the invention, and so as to improve the application properties of the resultant application mixture, the alkalizing composition preferably used according to the invention preferably comprises at least one surfactant in a total amount of 0.5 to 10 wt. %, and preferably 2 to 8 wt. %, each based on the weight thereof.

The surfactants suitable for the alkalizing compositions (Alk) that are preferably used according to the invention are selected from the same anionic, cationic, non-ionic, amphoteric and zwitterionic surfactants and emulsifiers that are disclosed above as surfactants and emulsifiers suitable for the oxidation compositions (Ox) that are preferably used.

Alkalizing compositions (Alk) that are particularly preferably used according to the invention furthermore comprise at least one oil and/or at least one fat component having a melting point in the range of 23 to 110° C., preferably in a total amount of 0.1 to 60 wt. %, particularly preferably 0.5 to 40 wt. %, and exceptionally preferably 2 to 24 wt. %, each based on the weight of the alkalizing composition (Ox) preferably used according to the invention. The oils suitable for the alkalizing compositions (Alk) that are preferably used according to the invention are the same oils disclosed above as suitable anti-dusting agents.

Fat components that are preferably used according to the invention in the alkalizing compositions (Alk) and have a melting point in the range of 23 to 110° C. are selected from linear saturated 1-alkanols having 12 to 30 carbon atoms, preferably in a total amount of 0.1 to 20 wt. %, particularly preferably 3 to 15 wt. %, and exceptionally preferably 5 to 10 wt. %, each based on the weight of the alkalizing composition used according to the invention.

The at least one linear saturated 1-alkanol having 12 to 30 carbon atoms is preferably selected from lauryl alcohol, myristyl alcohol, cetyl alcohol, stearyl alcohol, arachidyl alcohol and behenyl alcohol, and mixtures of these 1-alkanols, particularly preferably of cetyl alcohol, stearyl alcohol and cetyl alcohol/stearyl alcohol mixtures.

Alkalizing compositions (Alk) preferably used according to the invention furthermore comprise, each based on the weight thereof, at least one linear saturated 1-alkanol having 12 to 30 carbon atoms in a total amount of 0.1 to 20 wt. %, preferably in a total amount of 3 to 15 wt. %, and exceptionally preferably 5 to 10 wt. %, wherein at least one 1-alkanol, selected from cetyl alcohol, stearyl alcohol and cetyl alcohol/stearyl alcohol mixtures, is present.

Further preferred alkalizing compositions (Alk) used according to the invention comprise at least one fat component having a melting point in the range of 23 to 110° C. that is selected from esters of a saturated, monohydric $C_{16}$ to $C_{60}$ alkanol and a saturated $C_8$ to $C_{36}$ monocarboxylic acid, in particular cetyl behenate, stearyl behenate and $C_{20}$ to $C_{40}$ alkyl stearate, glycerol triesters of saturated linear $C_{12}$ to $C_{30}$ carboxylic acids, which may be hydroxylated, candelilla wax, carnauba wax, beeswax, saturated linear $C_{14}$ to $C_{36}$ carboxylic acids, and mixtures of the aforementioned substances.

Furthermore, the blonding powders according to the invention, or the preferred blonding powders according to the invention, and/or the alkalizing compositions preferably used according to the invention can contain at least one direct dye. These are dyes that attach directly to the hair and require no oxidative process to develop the color. Particularly preferably contain certain direct dyes of complementary colors are present for matting undesirable residual color impressions, in particular in the red or blue range, caused by decomposition products of melanin. Direct dyes are usually nitrophenylene diamines, nitroaminophenols, azo dyes, anthraquinones or indophenols. Direct dyes are known as anionic, cationic and non-ionic direct dyes. The respective direct dyes are preferably used in an amount of 0.001 to 2 wt. %, based on the blonding powder or the alkalizing composition (Alk).

Preferred anionic direct dyes are the compounds known under the international designations or trade names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, bromophenol blue and tetrabromophenol blue. Preferred cationic direct dyes are cationic triphenylmethane dyes, such as Basic Blue 7, Basic Blue 26, Basic Violet 2 and Basic Violet 14, aromatic systems substituted with a quaternary nitrogen group, such as Basic Yellow 57, Basic Red 76, Basic Blue 99, Basic Brown 16 and Basic Brown 17, cationic anthraquinone dyes such as HC Blue 16 (Bluequat B), and direct dyes that contain a heterocycle having at least one quaternary nitrogen atom, in particular Basic Yellow 87, Basic Orange 31 and Basic Red 51. The cationic direct dyes that are sold under the trademark Arianor are cationic direct dyes that are likewise preferred according to the invention. In particular non-ionic nitro and quinone dyes and neutral azo dyes are suited as non-ionic direct dyes. Preferred non-ionic direct dyes are the compounds known under the international designations or trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 11, Disperse Violet 1, Disperse Violet 4, Disperse Black 9, as well as 1,4-diamino-2-nitrobenzene, 2-amino-4-nitrophenol, 1,4-bis-(2-hydroxyethyl)-amino-2-nitrobenzene, 3-nitro-4-(2-hydroxyethyl)-aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 6-nitro-1,2,3,4-tetrahydroquinoxaline, 2-hydroxy-1,4-naphthoquinone, picramic acid and the salts thereof, 2-amino-6-chloro-4-nitrophenol, 4-ethylamino-3-nitrobenzoic acid and 2-chloro-6-ethylamino-4-nitrophenol. Especially particularly preferred according to the invention is a combination of tetrabromophenol blue and Acid Red 92.

The alkalizing composition preferably used according to the invention comprises at least one oxidation dye precursor, which is preferably selected from one or more developer components and optionally one or more coupler components, as a further optional ingredient.

Particularly preferably at least one oxidation dye precursor is present in a total amount of 0.0001 to 10.0 wt. %, and preferably 0.001 to 8 wt. %, each based on the weight of the alkalizing composition preferably used according to the invention.

It may be preferred according to the invention for the developer component to be at least one compound selected from the group formed of p-phenylenediamine, p-toluylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, N-(4-amino-3-methylphenyl)-N-[3-(1H-imidazole-1-yl)propyl]amine, N,N'-bis-(2-hydroxyethyl)-N,N'-bis-(4-aminophenyl)-1,3-diaminopropane-2-ol, bis(2-hydroxy-5-aminophenyl)methane, 1,3-bis-(2,5-diaminophenoxy)-propane-2-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol, 4-amino-2-(diethylaminomethyl)phenol, 4,5-diamino-1-(β-hydroxyethyl)pyrazole, 2,4,5,6-tetraaminopyrimidine, 4-hydroxy-2,5,6-triaminopyrimidine, 2-hydroxy-4,5,6-triaminopyrimidine, and the physiologically compatible salts thereof.

Preferably at least one developer component is present in a total amount of 0.0001 to 10.0 wt. %, and preferably 0.001 to 8 wt. %, each based on the weight of the alkalizing composition preferably used according to the invention.

Within the scope of oxidative dyeing, coupler components alone do not provide any significant coloration, but always require the presence of developer components. It is therefore preferred according to the invention to additionally use at least one coupler component when using at least one developer component.

According to the invention, preferred coupler components are selected from 3-aminophenol, 5-amino-2-methylphenol, N-cyclopentyl-3-aminophenol, 3-amino-2-chloro-6-methylphenol, 2-hydroxy-4-aminophenoxyethanol, 2,6-dimethyl-3-aminophenol, 3-trifluoroacetylamino-2-chloro-6-methylphenol, 5-amino-4-chloro-2-methylphenol, 5-amino-4-methoxy-2-methylphenol, 5-(2-hydroxyethyl)-amino-2-methylphenol, 3-(diethylamino)phenol, N-cyclopentyl-3-aminophenol, 1,3-dihydroxy-5-(methylamino)benzene, 3-ethylamino-4-methylphenol, 2,4-dichloro-3-aminophenol, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholine-4-ylphenyl)amino]ethanol, 3-amino-4-(2-methoxyethoxy)-5-methylphenylamine, 1-amino-3-bis-(2-hydroxyethyl)-aminobenzene, resorcinol, resorcinol monomethyl ether, 2-methylresorcinol, 5-methylresorcinol, 2,5-dimethylresorcinol, 2-chlororesorcinol, 4-chlororesorcinol, pyrogallol, 1,2,4-trihydroxybenzene, 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-4-methylpyridine, 2,6-diaminopyridine, 2,3-diamino-6-methoxypyridine, 3,5-diamino-2,6-dimethoxypyridine, 2,6-dihydroxy-3,4-dimethylpyridine, 3,4-diaminopyridine, 2-(2-methoxyethyl)amino-3-amino-6-methoxypyridine, 2-(4'-methoxyphenyl)amino-3-aminopyridine, 1-naphthol, 2-methyl-1-naphthol, 2-hydroxymethyl-1-naphthol, 2-hydroxyethyl-1-naphthol, 1,3-dihydroxynaphthalene, 1,5-dihydroxynaphthalene, 1,6-dihydroxynaphthalene, 1,7-dihydroxynaphthalene, 1,8-dihydroxynaphthalene, 2,7-dihydroxynaphthalene, 2,3-dihydroxynaphthalene, 4-hydroxyindole, 6-hydroxyindole, 7-hydroxyindole, 4-hydroxyindoline, 6-hydroxyindoline, 7-hydroxyindoline, 4,6-diaminopyrimidine, 4-amino-2,6-dihydroxypyrimidine, 2,4-diamino-6-hydroxypyrimidine, 2,4,6-trihydroxypyrimidine, 2-amino-4-methylpyrimidine, 2-amino-4-hydroxy-6-methylpyrimidine, and 4,6-dihydroxy-2-methylpyrimidine, or mixtures of these compounds or the physiologically compatible salts thereof.

Preferably at least one coupler component is present in a total amount of 0.0001 to 10.0 wt. %, and preferably 0.001 to 8 wt. %, each based on the weight of the alkalizing composition preferably used according to the invention.

The developer components and coupler components are generally used in approximately equimolar amounts relative to each other. While equimolar amounts have proven to be expedient, a certain excess of individual oxidation dye precursors is not disadvantageous, whereby developer components and coupler component can have a mole ratio of 0.2 to 2, and in particular 0.5 to 1.

The residence time is preferably 5 to 60 min, in particular 5 to 50 min, particularly preferably 10 to 45 min. During the residence time of the agents on the fiber, it may be advantageous to support the lightening or color changing process by supplying heat. A residence phase at room temperature is likewise covered by the invention. The temperature is in particular between 20° C. and 40° C., in particular between 25° C. and 38° C., during the exposure time. The agents already yield good treatment results at physiologically compatible temperatures of less than 45° C.

After the color changing process has ended, all components present on the keratin fibers are rinsed off the hair using water or a surfactant-containing cleansing agent. In particular commercially available shampoo may be used as the cleansing agent, wherein the cleansing agent can be dispensed with and the rinsing process can be carried out using tap water when the color changing agent has a higher surfactant content.

A further subject matter of the present invention is the use of a combination of at least one dicarboxylic acid having 2 to 10 carbon atoms, selected from succinic acid, malic acid, oxalic acid, malonic acid, adipic acid, pimelic acid, suberic acid, azelaic acid, sebacic acid, maleic acid, fumaric acid, D-tartaric acid, L-tartaric acid, meso-tartaric acid, racemic acid, alpha-ketoglutaric acid, beta-ketoglutaric acid, oxaloacetic acid, and/or at least one salt of these acids and mixtures of these compounds, wherein the dicarboxylic acid having 2 to 10 carbon atoms is preferably selected from succinic acid, malic acid, maleic acid and the salts of succinic acid, malic acid or maleic acid,
in combination with
at least one amino acid, selected from arginine, lysine, histidine or at least one of the salts of these amino acids, in a blonding powder that comprises at least one oxidizing agent, selected from sodium percarbonates and inorganic salts of a peroxosulfuric acid, and mixtures thereof, and furthermore 0 to 8 wt. % water, based on the weight of the blonding powder,
so as to reduce the damage to the keratin fibers, and in particular human hair, which is caused by treating the fibers with a mixture of the blonding powder and an oxidation composition, which, in each case based on the weight thereof, comprises 50 to 96 wt. %, preferably 70 to 93 wt. %, and particularly preferably 80 to 90 wt. % water and 0.5 to 20 wt. % hydrogen peroxide and has a pH value in the range of 2.5 to 5.5, measured at 20° C.

What was said above with respect to the blonding powders according to the invention, and the preferred blonding powders according to the invention applies, mutatis mutandis, also to the multi-component packing units (kits of parts) according to the invention, and the preferred multi-component packaging units (kits of parts) according to the invention.

What was said above with respect to the blonding powders according to the invention, and the preferred blonding powders according to the invention applies, mutatis mutandis, also to the methods according to the invention, and the preferred methods according to the invention, for lightening and/or changing the color of the keratin fibers.

What was said above with respect to the oxidation compositions or alkalizing compositions according to the invention, and the oxidation compositions or alkalizing compositions preferably used according to the invention applies, mutatis mutandis, also to the multi-component packing units (kits of parts) according to the invention, and the preferred multi-component packaging units (kits of parts) according to the invention.

What was said above with respect to the oxidation compositions or alkalizing compositions according to the invention, and the oxidation compositions or alkalizing compositions preferably used according to the invention applies, mutatis mutandis, also to the methods according to the invention, and the preferred methods according to the invention, for lightening and/or changing the color of the keratin fibers.

What was said above with respect to the blonding powders according to the invention, and the preferred blonding powders according to the invention applies, mutatis mutandis, also to the use according to the invention.

What was said above with respect to the oxidation compositions or alkalizing compositions according to the invention, and the oxidation compositions or alkalizing compositions preferably used according to the invention applies, mutatis mutandis, also to the use according to the invention.

EXAMPLES 1.1 Developer Emulsion

| Ingredient | Amount (wt. %) |
| --- | --- |
| Dipicolinic acid (2,6-pyridinedicarboxylic acid) | 0.1 |
| Potassium hydroxide | 0.15 |
| Etidronic acid | 0.2 |
| Sodium cetearyl sulfate | 0.4 |
| Cetearyl alcohol | 3.5 |
| PEG-40 castor oil | 0.8 |
| Paraffinum liquidum | 17.0 |
| Disodium pyrophosphate | 0.1 |
| Sodium benzoate | 0.04 |
| Hydrogen peroxide | 9.0 |
| Water | to make 100 |

1.2 Blonding Powder Formulations (unless indicated otherwise, the quantity information refers to percent by weight)

|  | No. 1 (V) | No. 2 (V) | No. 3 (E) | No. 4 (E) |
| --- | --- | --- | --- | --- |
| Potassium persulfate | 32.00 | 32.00 | 32.00 | 32.00 |
| Ammonium persulfate | 10.00 | 10.00 | 10.00 | 10.00 |
| Succinic acid | — | — | 1.00 | 2.00 |
| L-Arginine | — | 1.00 | 0.20 | 0.40 |
| Lysine hydrochloride | — | — | 0.20 | 0.40 |
| Sodium silicate with $SiO_2/Na_2O$ (molar) from 2.61 to 2.70 | 36.00 | 36.00 | 36.00 | 36.00 |
| Magnesium hydroxide carbonate | 13.45 | 10.25 | 10.35 | 8.95 |
| Sodium hexametaphosphate | 0.20 | 0.20 | 0.20 | 0.20 |
| Methylmethacrylat/Methacrylic acid copolymer | 1.00 | 1.00 | 1.00 | 1.00 |
| Carboxymethyl cellulose | 2.00 | 2.00 | 2.00 | 2.00 |
| EDTA Na2 | 0.60 | 0.60 | 0.60 | 0.60 |
| EDTA Na4 | — | 1.60 | 1.60 | 1.60 |
| Polyquaternium-10 | — | 0.50 | — | — |
| Hydrophilic silicic acid | 0.40 | 0.40 | 0.40 | 0.40 |
| CI 77007 (Ultramarines) | 0.15 | 0.15 | 0.15 | 0.15 |
| Paraffinum Liquidum | 3.60 | 4.30 | 4.30 | 4.30 |
| Perfume | 0.60 | 0.60 | 0.60 | 0.60 |
| Total | 100.00 | 100.00 | 100.00 | 100.00 |
| Difference in tensile strength (Young's modulus) after two blonding treatments ($\times 10^9$) | −(1.69 ± 0.22) | −(1.45 ± 0.13) | −(1.22 ± 0.12) | −(1.28 ± 0.12) |

The respective blonding powder and the developer emulsion were mixed with each other in a weight ratio of 1:2.

All blonding treatments resulted in a loss of tensile strength of the hair fiber. When compositions E3 and E4 according to the invention are used, however, this loss in tensile strength can statistically be significantly reduced.

2. Application 100 g of the freshly prepared mixture made of the respective blonding powder and the developer emulsion was applied to strands of dry hair (4 g application mixture per gram of hair).

After the strands were blonded for 45 minutes at 32° C., they were washed for 2 minutes with water and dried by way of a blow dryer.

This blonding process was repeated once more so that the strands were consecutively blonded twice in total.

3. Measurements of Hair Tensile Strength

Background

Young's modulus is also referred to as modulus of elasticity (elastic modulus). It corresponds to the ratio of stress to strain at linear elastic properties (in the range according to Hooke's law).

Hooke's law of elasticity describes the linear dependence of a body's change in longitude (strain) upon a deforming force (stress).

For moist hair, the linear correlation for strain is 0 to 2%.

Young's modulus is a measure of the strength of a fiber (the greater the value of the Young's modulus, the stronger is the fiber).

The strands used for the measurements consisted of 40 fibers (Kerling International (Backnang, Germany), European Natural Hair 7/0; batch #2014, mixture 138).

Initially, the average cross-sectional area of each individual hair is determined (Universal Dimension Measuring Device UDM 5000A, (Zimmer GmbH, Darmstadt)), and more particularly at a temperature of 22° C. and relative humidity of 50%. These values are needed for calculating the stress values.

3.2. Determining the Young's Modulus prior to Applying the Blonding Agent

All hair fibers were soaked in water for one hour. Afterwards, they were strained using the MTT 680 stress-strain system comprising a UV 1000 control unit (Dia-Stron Ltd, UK) at a constant speed of 10 mm/min. within the elastic phase (0 to 1.5% extension). Afterwards, the modulus of elasticity (Young's modulus) was calculated (software: UvWin 1.32.1000 (Dia-Stron Ltd, UK).

3.3. Determining the Young's Modulus after Applying the Blonding Agent

After the four blonding treatments, the hair fibers were stored for at least 48 hours.

The hair fibers were soaked in water for one hour. Afterwards, they were strained using the MTT 680 stress-strain system comprising a UV 1000 control unit (Dia-Stron Ltd, UK) at a constant speed of 10 mm/min. within the elastic phase (0 to 1.5% extension). Afterwards, the modulus of elasticity (Young's modulus) was calculated (software: UvWin 1.32.1000 (Dia-Stron Ltd, UK).

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. An anhydrous blonding powder, comprising:
   a) at least one oxidizing agent, selected from the group consisting of sodium peroxodisulfate, potassium peroxodisulfate, ammonium peroxodisulfate, and mixtures thereof, wherein the oxidizing agent is present in a total amount of 5 to 85 wt. % based on the weight of the blonding powder;
   b) succinic acid present in the amount of 0.03 to 7 wt. % based on the weight of the blonding powder; and
   c) at least one amino acids selected from the group consisting of arginine, lysine, and histidine, and at least one of a salt of an amino acid selected from the group consisting of arginine, lysine, and histidine wherein the amino acid and salt are present in a total amount, converted to the mass of free amino acid, of 0.1 to 7 wt. % based on the weight of the blonding powder.

2. An anhydrous blonding powder according to claim 1, further including at least one inorganic alkalizing agent that is solid at 20° C. and 1013 mbar, in a total amount of 1 to 60 wt. %, based on the weight of the blonding powder.

3. An anhydrous powder according to claim 1, further including at least one oil in a total amount of 0.1 to 15 wt. % based on the weight of the blonding powder.

4. An anhydrous blonding powder according to claim 1, further comprising at least one complexing agent in a total amount of 0.1 to 3 wt. % based on the weight of the blonding powder, the at least one complexing agent selected from the group consisting of ethylenediaminetetraacetic acid (EDTA), N-hydroxyethyl ethylenediaminetriacetic acid, aminotrimethylene phosphonic acid, diethylenetriaminepentaacetic acid, lauroyl ethylenediaminetriacetic acid, nitrilotriacetic acid, iminodisuccinic acid, N-2 hydroxyethyl iminodiacetic acid, ethylene glycol-bis-(beta-aminoethyl ether)-N,N-tetraacetic acid; pentasodium aminotrimethylene phosphonate, salts thereof, and mixtures thereof.

5. An anhydrous blonding powder of claim 1 wherein the amino acid is arginine and the salt of the amino acid is lysine hydrochloride.

6. A method for lightening human hair comprising:
   mixing the anhydrous blonding powder (B) according to claim 1 with an oxidation composition (Ox), which based on the weight thereof includes 50 to 96 wt. % hydrogen peroxide, and
   further including at least one pH setting agent in an amount that the oxidation composition has a pH value in the range of 2.5 to 5.5, measured at 20° C., immediately thereafter applying the mixture to the hair for 5 to 60 minutes, and
   rinsing the hair with water, and optionally with a surfactant-containing cleansing agent,
   wherein the anhydrous blonding powder (B) and the oxidation composition (Ox) are mixed with each other in a weight-based ratio (B):(Ox) of 0.2 to 1.

* * * * *